(12) United States Patent
Gao et al.

(10) Patent No.: US 9,089,398 B2
(45) Date of Patent: Jul. 28, 2015

(54) ASPIRATION CASSETTE WITH GAS AND DEBRIS MANAGEMENT

(71) Applicants:Shawn X. Gao, Irvine, CA (US); Roderick S. Van, Long Beach, CA (US)

(72) Inventors: Shawn X. Gao, Irvine, CA (US); Roderick S. Van, Long Beach, CA (US)

(73) Assignee: Alcon Research, Ltd., Fort Worth, TX (US)

( * ) Notice: Subject to any disclaimer, the term of this patent is extended or adjusted under 35 U.S.C. 154(b) by 200 days.

(21) Appl. No.: 13/621,571

(22) Filed: Sep. 17, 2012

(65) Prior Publication Data

US 2014/0081224 A1    Mar. 20, 2014

(51) Int. Cl.
*A61M 1/00*    (2006.01)
*A61F 9/007*    (2006.01)

(52) U.S. Cl.
CPC .......... *A61F 9/00736* (2013.01); *A61M 1/0058* (2013.01); *A61M 2205/123* (2013.01); *A61M 2205/3306* (2013.01); *A61M 2205/3389* (2013.01); *A61M 2210/0612* (2013.01)

(58) Field of Classification Search
CPC .......... A61F 9/00736; A61M 2205/12; A61M 2205/123
USPC .............................. 604/319, 9, 326, 541–542
See application file for complete search history.

(56) References Cited

U.S. PATENT DOCUMENTS

| | | | |
|---|---|---|---|
| 4,475,904 A * | 10/1984 | Wang | 604/119 |
| 4,758,238 A | 7/1988 | Sundblom et al. | |
| 4,798,090 A * | 1/1989 | Heath et al. | 73/715 |
| 5,267,956 A | 12/1993 | Beuchat | |
| 5,298,020 A * | 3/1994 | Stone | 604/6.05 |
| 5,800,396 A | 9/1998 | Fanney et al. | |
| 5,910,110 A * | 6/1999 | Bastable | 600/398 |
| 6,319,223 B1 | 11/2001 | Wortrich et al. | |
| 6,908,451 B2 | 6/2005 | Brody et al. | |
| 6,991,615 B2 * | 1/2006 | Villafana et al. | 604/9 |
| 7,238,010 B2 | 7/2007 | Hershberger et al. | |
| 7,244,240 B2 | 7/2007 | Nazarifar et al. | |
| 7,393,189 B2 | 7/2008 | Davis et al. | |

(Continued)

FOREIGN PATENT DOCUMENTS

| | | |
|---|---|---|
| EP | 0362822 A2 | 4/1990 |
| WO | 2013019297 A1 | 2/2013 |
| WO | 2014042817 A1 | 3/2014 |

OTHER PUBLICATIONS

International Searching Authority, International Search Report, PCT/US2013/055301, Nov. 13, 2013, 2 pages.

(Continued)

*Primary Examiner* — Philip R Wiest
*Assistant Examiner* — Ariana Zimbouski

(57) ABSTRACT

Embodiments of this disclosure provide an apparatus and method for gas and debris management. The apparatus comprises a surgical cassette, wherein the surgical cassette is at least partially formed of a cassette material defining a chamber. The surgical cassette has a floor and a plurality of walls. The apparatus also has a drain conduit with a drain entry and a drain exit. The drain entry is connected to the chamber near the floor. The drain conduit has a top portion and a bottom portion. The apparatus also has an aspiration conduit. The aspiration conduit has an aspiration port and an aspiration exit. The aspiration conduit is in liquid communication with the chamber and the drain conduit. At least a portion of the top portion of the drain conduit is positioned above at least a portion of the aspiration exit.

5 Claims, 7 Drawing Sheets

(56) References Cited

U.S. PATENT DOCUMENTS

| | | |
|---|---|---|
| 7,604,615 B2 | 10/2009 | Gao et al. |
| 7,780,633 B2 | 8/2010 | Domash |
| 7,896,839 B2 | 3/2011 | Nazarifar et al. |
| 7,942,853 B2 | 5/2011 | Svetic |
| 8,048,047 B2 | 11/2011 | Domash |
| 8,172,832 B1 * | 5/2012 | Gonzalez ............ 604/542 |
| 8,202,243 B2 | 6/2012 | Morgan |
| 8,398,582 B2 | 3/2013 | Gordon et al. |
| 2007/0098579 A1 | 5/2007 | Boukhny et al. |
| 2007/0207041 A1 * | 9/2007 | Gao et al. ............ 417/53 |
| 2008/0147023 A1 | 6/2008 | Hopkins et al. |
| 2012/0157912 A1 | 6/2012 | Sorensen et al. |
| 2014/0081224 A1 | 3/2014 | Gao et al. |

OTHER PUBLICATIONS

International Searching Authority, Written Opinion of the International Searching Authority, PCT/US2013/55301, Nov. 13, 2013, 6 pages.

* cited by examiner

ASPIRATION CASSETTE WITH GAS AND DEBRIS MANAGEMENT

BACKGROUND

During small incision surgery, and particularly during ophthalmic surgery, small probes are inserted into the operative site to cut, remove, or otherwise manipulate tissue. During these surgical procedures, fluid is typically infused into the eye, and the infusion fluid and tissue are aspirated from the surgical site. The aspirated fluids from the surgical site are at least partially drawn into an aspiration chamber located within a surgical cassette. The level of aspirated fluids in the aspiration chamber is measured using a non-invasive level sensor. In prior systems, gas and debris in the aspirated fluids enter the aspiration chamber, which results in the level sensor producing inaccurate readings. This can cause certain problems. Therefore, a need continues to exist for an improved aspiration cassette with gas and debris management.

SUMMARY

The present disclosure relates in general to an apparatus having an aspiration cassette with gas and debris management and more particularly to an aspiration cassette for an ophthalmic microsurgical system that prevents gas or debris within aspiration liquid from entering an aspiration chamber of the aspiration cassette. In one embodiment, an apparatus has a chamber having a floor and a plurality of walls. The apparatus also has a drain conduit, the drain conduit having a drain entry and a drain exit, wherein the drain entry is connected to the chamber near the floor. The drain conduit also has a top portion and a bottom portion. The apparatus also has an aspiration conduit in liquid communication with the chamber and the drain conduit, wherein the aspiration conduit has an aspiration port and an aspiration exit, and wherein at least a top portion of the drain conduit is positioned above at least a portion of the aspiration exit.

DETAILED DESCRIPTION

Figure 1:
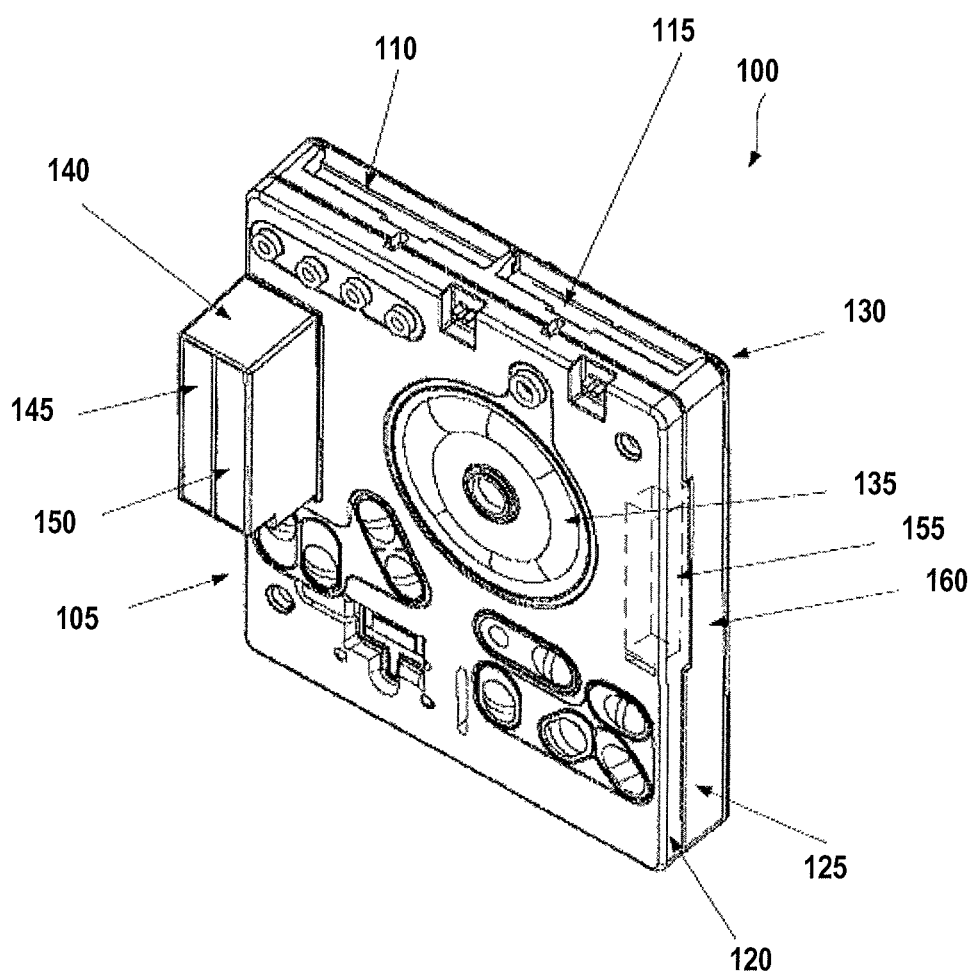
FIG. 1 is a diagrammatic representation of one embodiment of a liquid cassette.

The following disclosure provides many different embodiments or examples. Specific examples of components and arrangements are described below to simplify the present disclosure. These are, of course, merely examples and are not intended to be limiting. In addition, the present disclosure may repeat reference numerals and/or letters in the various examples. This repetition is for the purpose of simplicity and clarity and does not in itself dictate a relationship between the various embodiments and/or configurations discussed.

In an exemplary embodiment, as illustrated in FIG. 1, a diagrammatic representation of a liquid cassette is generally referred by the reference numeral 100. The cassette 100 can provide a closed system fluidic device that can be discarded following a surgical procedure. A surgical procedure is generally performed on a human body and typically involves forming a passage through an external surface of the body, but can also be performed through a natural orifice. The cassette 100 can include a cassette body 105 and portions that interface with a clamp (e.g., indicated generally at clamping zones 110 and 115) projecting from the cassette body 105. The cassette 100 can be formed of ABS plastic or other suitable material. In the embodiment shown, the cassette 100 is formed from three primary sections: an inner or surgical console interface section 120 that faces an ophthalmic surgical console 500 (shown in FIG. 5) when the cassette 100 is inserted into the ophthalmic surgical console, a middle section 125, and a cover plate 130. The various sections of the cassette 100 can be coupled together via a press fit, interlocking tabs, chemical bonding, thermal bonding, mechanical fasteners or other attachment mechanism known in the art. In other embodiments, the cassette 100 can be formed of a single piece or multiple pieces.

The surgical console interface section 120 can face the console 500 during use and provide an interface for liquid flow channels (e.g., flow channel 135 for the peristaltic pump provided by an elastomeric pump membrane), valves (e.g., infusion/aspiration valves), and other features to manage liquid flow. The cassette 100 can also attach to a drain bag (not shown) to collect liquids during a procedure.

In one embodiment, the liquid cassette 100 is formed of a cassette material formed to create chambers to hold liquids for aspiration and infusion. For example, chamber cartridge 140 can include two infusion chambers 145 and 150. An aspiration chamber 155 can be internal to the cassette 100 on the opposite side of the cassette 100 from the chamber cartridge 140 (e.g., at the side of cassette 100 indicated by 160). According to one embodiment, the level of liquid in the chambers can be determined in a noninvasive manner. As described below, light can be projected into the walls of each of the chambers 145, 150 and 155 using a vertical light source (not shown). Depending on the reflection or refraction of light at the chambers 145, 150, and 155, a vertical sensor array will detect or not detect light at various points along the array's vertical axis. Based on the transition between illuminated and non illuminated portions of the sensor array, the level of the liquid in each of the chambers 145, 150, and 155 can be detected. One embodiment of a non-invasive method of measuring the liquid in the chambers is described in U.S. Pat. No. 7,956,341 to Gao, which is hereby fully incorporated by reference herein.

Figure 2:
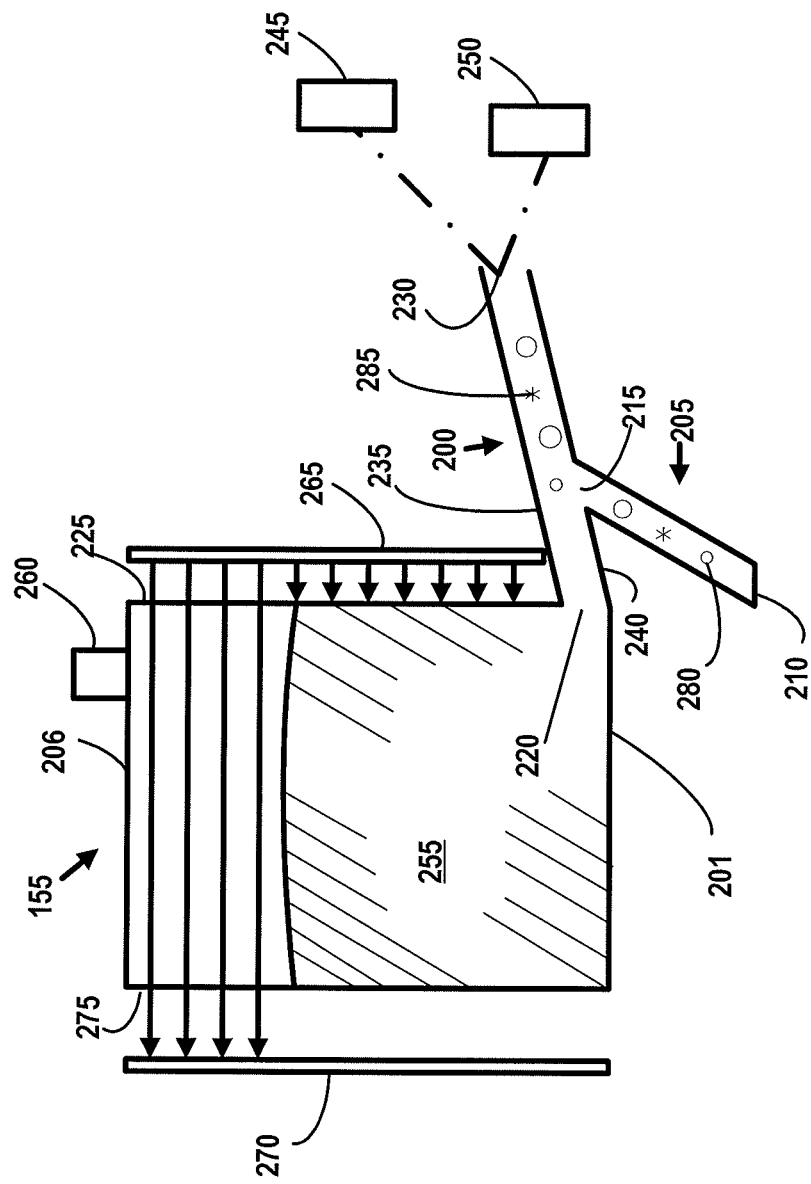
FIG. 2 is a diagrammatic representation of an aspiration chamber configuration within the liquid cassette of FIG. 1, according to an exemplary embodiment.

FIG. 2 is a diagrammatic representation of the chamber 155 having a drain conduit 200 extending from a floor 201 of the chamber 155 and an aspiration conduit 205 coupled thereto. The chamber 155 has a top 206. The chamber 155 is in liquid communication with the aspiration conduit 205 and the drain conduit 200. On one end, the aspiration conduit 205 has an aspiration port 210 which can be attached to a surgical device (not shown) used to remove liquid and other matter from a surgical site (not shown). The aspiration conduit 205 has an aspiration exit 215 located at an opposing end. The aspiration exit 215 is fluidly coupled to the chamber 155 and the drain conduit 200, therefore the aspiration conduit 205 is in liquid communication with the chamber 155 and the drain conduit 200. The drain conduit 200 has a drain entry 220 that is located on one end portion of the drain conduit 200, with the drain entry 220 being attached to a chamber wall 225. A drain exit 230 is located at an opposing end of the drain conduit 200. The drain conduit 200 also has a top portion 235 and a bottom portion 240. The drain exit 230 is configured to be attached to a drain bag 245 and coupled to a drain pump 250, which if activated, can draw a liquid 255 through the aspiration port 210 and towards the drain bag 245. The chamber 155 is configured to attach to a chamber pump 260. The level of the liquid 255 in the chamber 155 is measured using a light source 265 and a sensor 270. In one embodiment, the portions of the wall 225 and a wall 275 that face the light source 265 and the sensor 270 are transparent or opaque. The sensor 270 receives some portion of the light projected by the light source 265 and outputs a signal indicating the amount of light received at various portions of the sensor 270 (e.g., at various pixels of the array). In one embodiment, an edge detection scheme is applied to the output of the sensor 270 to determine which portions of the linear sensor array are sufficiently illuminated to indicate the presence/absence of the liquid 255 at the corresponding level in the chamber 155. According to one embodiment, the output of different portions of the sensor 270 are compared with a threshold to determine if that portion of the sensor 270 is in a first state (e.g., associated with air) or in a second state (e.g., associated with the liquid). The transition between the first state and second state portions of the linear sensor array marks the level of the liquid 255. It should be noted however, other edge detection mechanisms can be employed, such as linear interpolation. Introduction of a gas 280 or other matter, such as debris 285, into the liquid 255 can affect the accuracy of the sensor 270. Accordingly, preventing the gas 280 or the debris 285 from entering the chamber 155 improves the accuracy of the sensor 270.

Figure 3A:
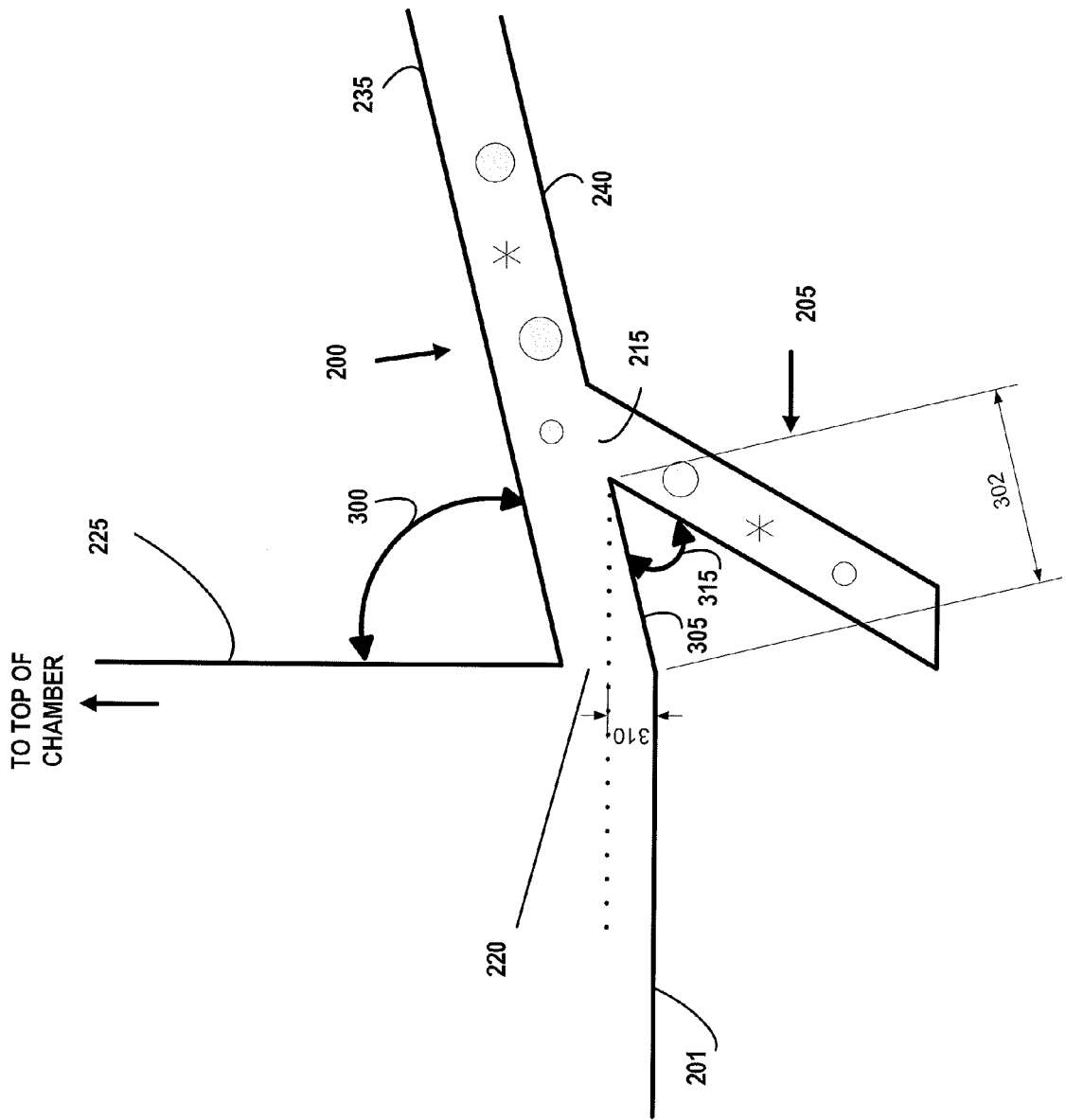
FIG. 3A is an enlarged portion of the diagrammatic representation of FIG. 2, according to an exemplary embodiment.

In one embodiment and as shown in FIG. 3A, the drain entry 220 is attached to the chamber 155 with the drain conduit 200 extending upwards from near the floor 201 of the chamber 155. The intersection of the top portion of the drain conduit 235 and the chamber wall 225 forms a nonorthogonal, acute angle 300 between the top portion of the drain conduit 235 and the chamber wall 225. Additionally, the aspiration conduit 205 is attached to the drain conduit 200 with the aspiration exit 215 intersecting the bottom portion of the drain conduit 240. The intersection of the drain conduit 200 and the aspiration conduit 205 is offset from the wall 225 by a first distance 302 along the bottom portion of the drain conduit 240 defining a first portion 305. The intersection of the drain conduit 200 and the aspiration conduit 205 is offset above the drain entry 220 and towards the top of the chamber 206 by a second distance 310. That is, the intersection of the drain conduit 200 and the aspiration conduit 205 is located above the floor 201 and towards the top 206 of the chamber 155. A nonorthogonal, acute angle 315 is defined at the intersection of the first portion 305 and the aspiration conduit 205. The acute angle 315 is an acute angle to minimize turbulence flow of the liquid 255 towards the chamber 155 at the aspiration exit 215.

Figure 3B:
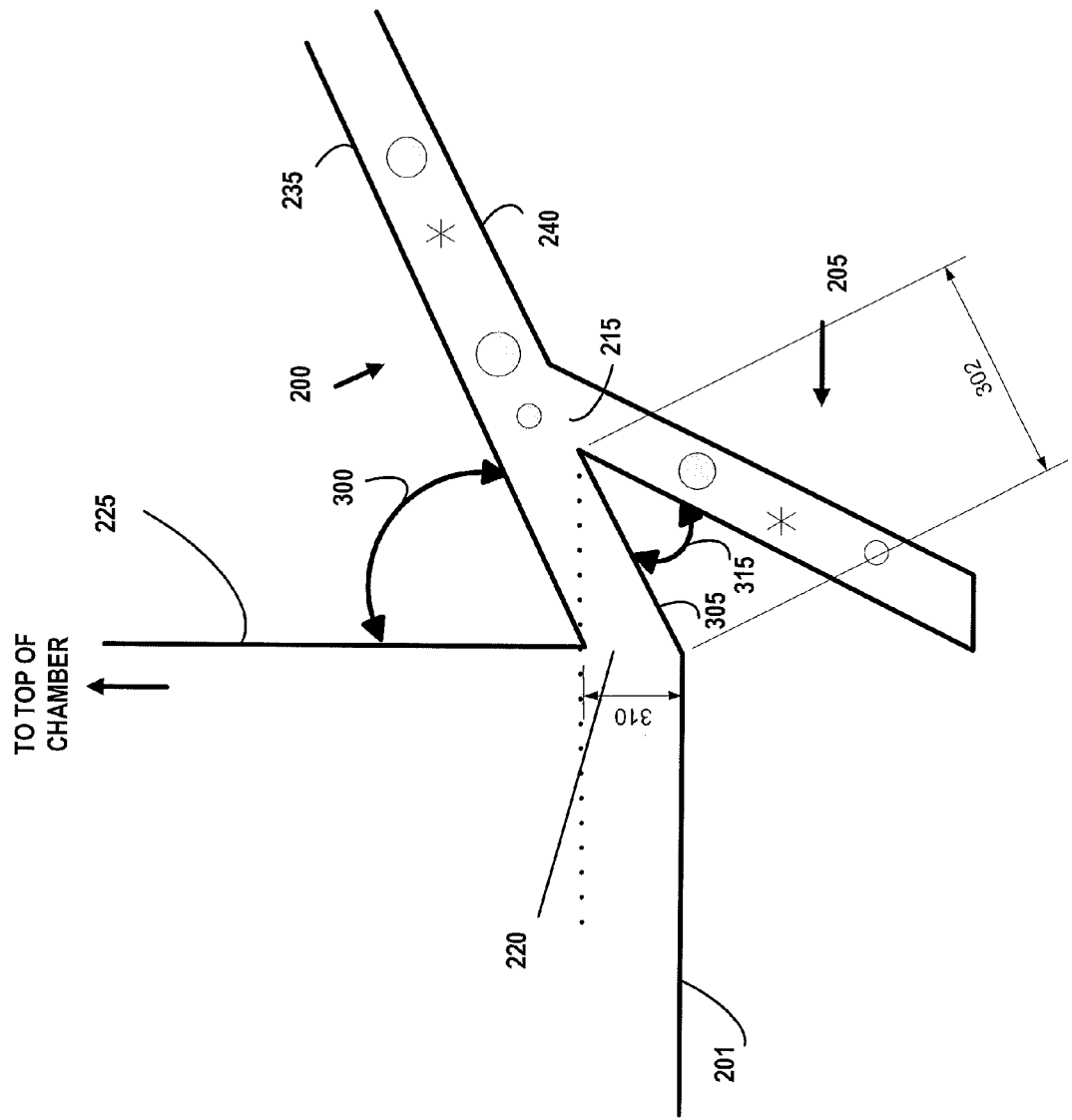
FIG. 3B is an enlarged portion of the diagrammatic representation of FIG. 2, according to an exemplary embodiment.

In another embodiment, as shown in FIG. 3B, the acute angle 300 and the first distance 302 along the bottom portion of the drain conduit 240 is such that the second distance 310 is equal to or greater than the height or opening of the drain entry 220.

Figure 4:
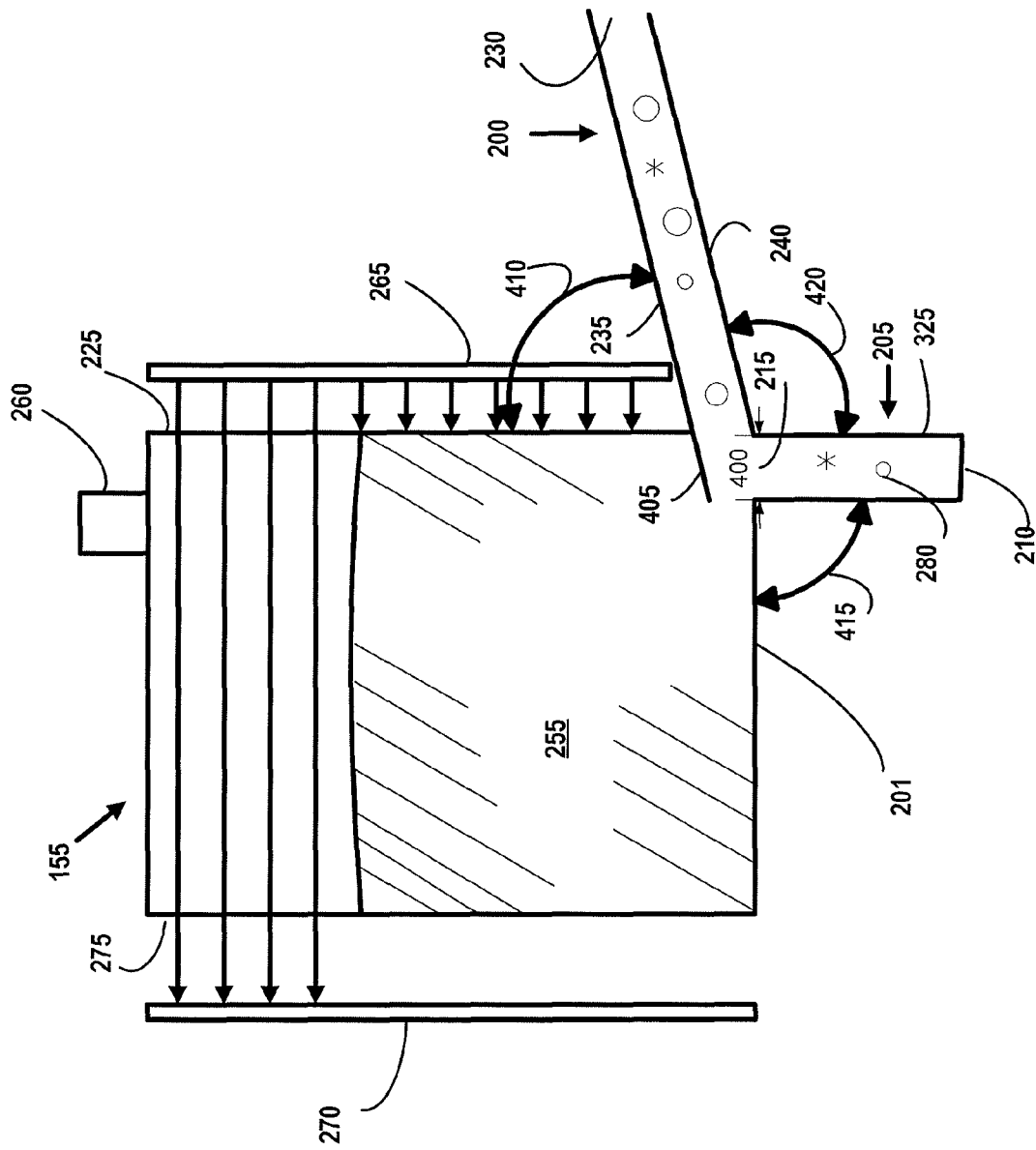
FIG. 4 is another diagrammatic representation of an aspiration chamber configuration within the liquid cassette of FIG. 1, according to an exemplary embodiment.

In another embodiment, as shown in FIG. 4, the aspiration conduit 205 can be attached to the chamber 155 near the floor 201 of the chamber 155. The aspiration exit 215 can have an opening 400. The top portion of the drain conduit 235 extends within the chamber 155 to form an exit cover 405. The exit cover 405 has a length and at least partially covers the aspiration exit opening 400. In one embodiment, the length of the exit cover 405 is the same measurement as the aspiration exit opening 400. In one embodiment, the length of the cover 405 extends over the exit opening 400. The top portion of the drain conduit 235 intersects the chamber wall 225 to define a nonorthogonal, acute angle 410 between the top portion of the drain conduit 235 and the chamber wall 225. The aspiration conduit 205 intersects the floor 201 to form an angle 415 between the aspiration conduit 205 and the floor 201. In one embodiment, the angle 415 is an acute angle to minimize turbulence flow of the liquid 255 towards the chamber 155 at the aspiration exit 215. In one embodiment, the angle 415 is a right angle. The aspiration conduit 205 intersects the drain conduit 200 to define an obtuse angle 420 between the aspiration conduit 205 and the bottom portion of the drain conduit 240. The intersection of the aspiration conduit 205 and the bottom portion of the drain conduit 240 is not offset from the floor 201. The aspiration exit opening 400 is located inside of the chamber 155. In one embodiment, the aspiration exit opening 400 is at least partially located inside of the chamber 155.

Figure 5:
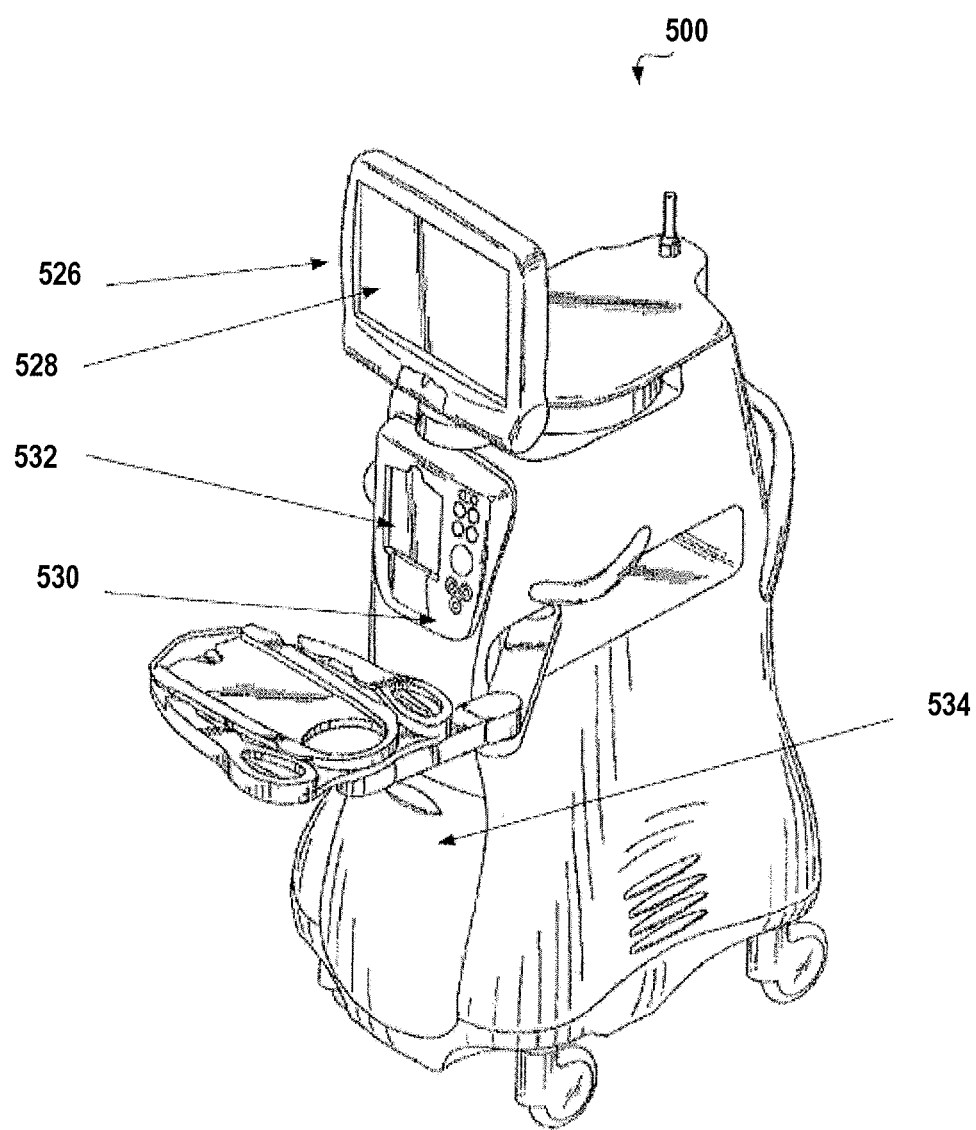
FIG. 5 is a diagrammatic representation of one embodiment of a surgical console; and, FIG. 6 is a diagrammatic representation of one embodiment of a cassette receiver.

In an exemplary embodiment, as illustrated in FIG. 5, the ophthalmic surgical console is generally referred to by the reference numeral 500. The surgical console 500 can include a swivel monitor 526 that has a touch screen 528. The swivel monitor 526 can be positioned in a variety of orientations for whomever needs to see the touch screen 528. The swivel monitor 526 can swing from side to side, as well as rotate and tilt. The touch screen 528 provides a graphical user interface ("GUI") that allows a user to interact with the console 500.

The surgical console 500 also includes a connection panel 530 used to connect various tools and consumables to the surgical console 500. The connection panel 530 can include, for example, a coagulation connector, connectors for various hand pieces, and a cassette receiver 532. The surgical console 500 can also include a variety of user friendly features, such as a foot pedal control (e.g., stored behind panel 534) and other features.

In operation, the cassette 100 can be placed in the cassette receiver 532. A clamp in the surgical console 500 clamps the cassette 100 in place to minimize movement of the cassette 100 during use. The clamp can clamp the top and bottom of the cassette 100, the sides of the cassette 100 or otherwise clamp the cassette 100.

Figure 6:
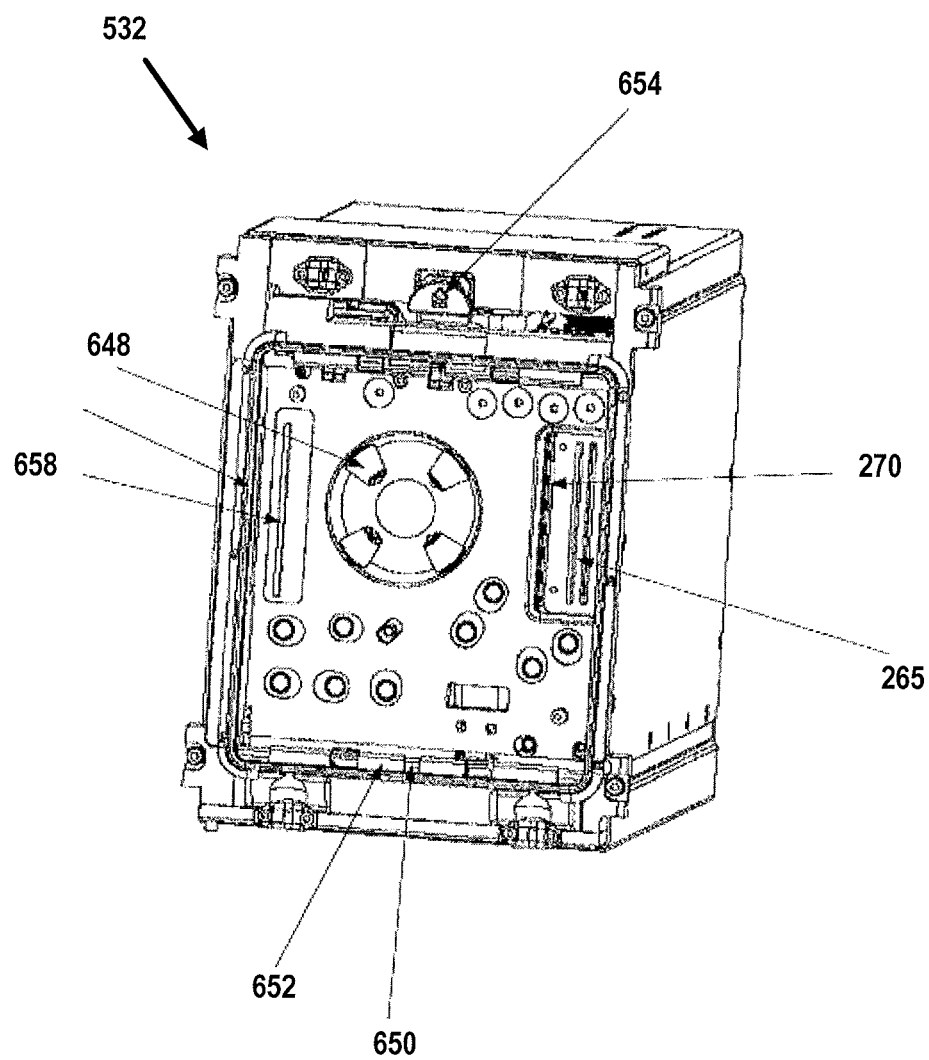

FIG. 6 is a diagrammatic representation of one embodiment of the cassette receiver 532 without a cassette 100. The cassette receiver 532 can have various pneumatic input and output ports to interface with the liquid cassette 100. The cassette receiver 532 can further include an opening to allow peristaltic pump rollers 648 to contact the liquid cassette 100 during operation. One embodiment of a peristaltic pump and complimentary cassette is described in U.S. Pat. No. 6,293, 926 to Sorensen, which is hereby fully incorporated by reference herein.

The liquid cassette receiver 532, in the embodiment of FIG. 6, is configured to hold the cassette 100 in place by a clamp having a bottom rail 650 and a top rail (not shown). Each rail can have outer clamping fingers (e.g., clamp finger 652) that contact the cassette 100 in corresponding clamping zones and inner clamping fingers to locate the cassette 100 during insertion and push the cassette 100 out of the cassette receiver 532 during release. A release button 654 is pressed to initiate release of the cassette 100 from the clamp. The cassette receiver 532 can include the linear light source 265 and a linear light source 658. The linear light source 265 projects light onto the walls of the cassette chamber 155 and the sensor array 270 to detect the light refracted through the chamber wall 225. Each linear light source 265 can include a plurality of light sources vertically arranged (i.e., to project light along vertically spaced transmission paths) and positioned to project light onto a wall of the chamber 155. Respective linear sensor arrays can receive light refracted through the chamber or reflected at the chamber surface.

The configuration of FIG. 6 is provided by way of example. The form factor of the cassette receiver 532, placement and number of input/output ports and other features of the cassette receiver 532 can depend on the surgical console 500, surgical procedure being performed, or other factors.

In operation, the aspiration conduit 205, the drain conduit 200, and the chamber 155 is at least partially filled with the liquid 255. The chamber pump 260 is activated to draw the liquid 255 from the surgical site through the aspiration port 210. The drain pump 250 is activated to remove at least some of the liquid 255. In one embodiment, the drain pump 250 can be activated by the level sensor 270. The liquid 255 often contains the gas 280 and the debris 285, which if introduced into the chamber 155, can result in the sensor 270 producing inaccurate results due to the gas 280 and the debris 285 creating turbulence within the liquid 255, interfering the level sensing light, or creating bubbles and or foam near a top surface of the liquid 255 within the chamber 155. The gas 280 and the debris 285 can be introduced into the liquid 255 due to improper surgical technique, un-primed or leaky probes or hand pieces, etc.

In operation and referring to FIGS. 2 and 3A or 3B, coupling the aspiration exit 215 to the bottom portion of the drain conduit 240 can reduce the amount of gas 280 and debris 285 introduced into the chamber 155. When the drain pump 250 is activated, the force on the liquid 255 from the drain pump 250 overcomes the force on the liquid 255 from the chamber pump 260, therefore, the liquid 255, along with the gas 280 and debris 285 flows away from the aspiration port 210 and towards the drain bag 245. Buoyancy forces in the gas 280 will force the gas 280 away from the aspiration port 210 and pull it upwards. Locating the intersection of the aspiration conduit 205 and drain conduit 200 above the drain entry 220 and away from the chamber 155 by a first portion 305 encourages gas 280 and debris 285 to flow upwards with its buoyancy force towards the drain bag 245. Due to the acute angle 300 and the buoyancy forces in the gas 280, the gas will naturally flow through the drain conduit 200 towards the drain bag 245 and away from the chamber 155. The acute angle 315 reduces turbulence within the fluid 255 at the intersection of the aspiration conduit 205 and the drain conduit 200 and directs the flow of the liquid 255 towards the drain bag 245 and away from the chamber 155. Any gas 280 and debris 285 within the liquid 255 also flows towards the drain bag 245 and away from the chamber 155.

In operation and referring to FIG. 4, coupling the aspiration exit 215 to the bottom portion of the drain conduit 240 and the floor 201 can also reduce the amount of gas 280 and debris 285 introduced into the chamber 155. While the intersection of the aspiration conduit 205 and drain conduit 200 is not located above and away from the chamber floor 201, due to the acute angle 410 and the buoyancy forces in the gas 280, the gas will naturally flow through the drain conduit 200 towards the drain bag 245 and away from the chamber 155. The exit cover 405 directs the gas 280 and debris 285 towards the drain bag 245.

It is understood that variations may be made in the foregoing without departing from the scope of the present disclosure.

In several exemplary embodiments, the elements and teachings of the various illustrative exemplary embodiments may be combined in whole or in part in some or all of the illustrative exemplary embodiments. In addition, one or more of the elements and teachings of the various illustrative exemplary embodiments may be omitted, at least in part, and/or combined, at least in part, with one or more of the other elements and teachings of the various illustrative embodiments.

Any spatial references such as, for example, "upper," "lower," "above," "below," "between," "bottom," "vertical," "horizontal," "angular," "upwards," "downwards," "side-to-side," "left-to-right," "right-to-left," "top-to-bottom," "bottom-to-top," "top," "bottom," "bottom-up," "top-down," etc., are for the purpose of illustration only and do not limit the specific orientation or location of the structure described above.

In several exemplary embodiments, while different steps, processes, and procedures are described as appearing as distinct acts, one or more of the steps, one or more of the processes, and/or one or more of the procedures may also be performed in different orders, simultaneously and/or sequentially. In several exemplary embodiments, the steps, processes and/or procedures may be merged into one or more steps, processes and/or procedures.

In several exemplary embodiments, one or more of the operational steps in each embodiment may be omitted. Moreover, in some instances, some features of the present disclosure may be employed without a corresponding use of the other features. Moreover, one or more of the above-described embodiments and/or variations may be combined in whole or in part with any one or more of the other above-described embodiments and/or variations.

Although several exemplary embodiments have been described in detail above, the embodiments described are exemplary only and are not limiting, and those skilled in the art will readily appreciate that many other modifications, changes and/or substitutions are possible in the exemplary embodiments without materially departing from the novel teachings and advantages of the present disclosure. Accordingly, all such modifications, changes and/or substitutions are intended to be included within the scope of this disclosure as defined in the following claims. In the claims, any means-plus-function clauses are intended to cover the structures described herein as performing the recited function and not only structural equivalents, but also equivalent structures.

What is claimed is:

1. An apparatus comprising:
    a surgical cassette, wherein the surgical cassette is at least partially formed of a cassette material defining a chamber, the chamber having a floor and a plurality of walls;
    a drain conduit having a drain entry and a drain exit, the drain entry connected to the chamber near the floor, the drain conduit having a top portion and a bottom portion; and
    an aspiration conduit having an aspiration port and an aspiration exit directly exiting into the drain conduit, wherein the aspiration exit is separated from the chamber by the bottom portion of the drain conduit, and wherein the aspiration conduit is in liquid communication with the chamber through the bottom portion of the drain conduit; and
    wherein at least a portion of the top portion of the drain conduit is positioned above at least a portion of the aspiration exit; and
    wherein the bottom portion of the drain conduit is located below both the aspiration exit and the top portion of the drain conduit;
    wherein the apparatus further comprises:

a chamber pump coupled to the chamber for pulling a first vacuum on the chamber; and
a drain pump coupled to the drain exit for pulling a second vacuum on the drain conduit;
wherein fluid from the aspiration conduit flows into the chamber during operation of the chamber pump; and
wherein fluid from the aspiration conduit flows into the drain exit during operation of the drain pump.

2. The apparatus of claim 1, wherein the aspiration exit intersects the bottom portion of the drain conduit.

3. The apparatus of claim 2, wherein the intersection of the aspiration exit and the bottom portion of the drain conduit is located outside of the chamber.

4. The apparatus of claim 3,
wherein the intersection is offset from one of the plurality of walls of the chamber by a first distance;
wherein the aspiration exit is offset above the drain entry by a second distance; and
wherein a non-orthogonal acute angle is formed at the intersection between the bottom portion and the aspiration conduit.

5. The apparatus of claim 1, wherein the drain conduit extends away from one of the plurality of walls of the chamber to form a non-orthogonal acute angle between the drain conduit and the one of the plurality of walls of the chamber.

* * * * *